(12) United States Patent
Li et al.

(10) Patent No.: US 11,875,882 B1
(45) Date of Patent: Jan. 16, 2024

(54) SYSTEM FOR PREDICTING END-STAGE RENAL DISEASE COMPLICATION RISK BASED ON CONTRASTIVE LEARNING

(71) Applicant: ZHEJIANG LAB, Zhejiang (CN)

(72) Inventors: Jingsong Li, Hangzhou (CN); Feng Wang, Hangzhou (CN); Shengqiang Chi, Hangzhou (CN); Yu Tian, Hangzhou (CN); Tianshu Zhou, Hangzhou (CN)

(73) Assignee: ZHEJIANG LAB, Hangzhou (CN)

( * ) Notice: Subject to any disclaimer, the term of this patent is extended or adjusted under 35 U.S.C. 154(b) by 0 days.

(21) Appl. No.: 18/352,216

(22) Filed: Jul. 13, 2023

(30) Foreign Application Priority Data

Jul. 18, 2022 (CN) .......................... 202210838416.5

(51) Int. Cl.
*G16H 50/20* (2018.01)
*G16H 50/30* (2018.01)

(52) U.S. Cl.
CPC ............. *G16H 50/20* (2018.01); *G16H 50/30* (2018.01)

(58) Field of Classification Search
None
See application file for complete search history.

(56) References Cited

U.S. PATENT DOCUMENTS

| 11,610,679 | B1 * | 3/2023 | Zhan | ........................ | G06N 3/096 |
| 2008/0146893 | A1 | 6/2008 | Levendowski et al. | | |
| 2021/0183471 | A1 * | 6/2021 | Cha | ........................ | G16H 50/30 |

FOREIGN PATENT DOCUMENTS

| CN | 110827993 A | 2/2020 |
| CN | 111933284 A | 11/2020 |
| CN | 112036515 A | 12/2020 |
| CN | 112508580 A | 3/2021 |
| CN | 112530594 A | 3/2021 |
| CN | 113178258 A | 7/2021 |
| CN | 114386454 A | 4/2022 |
| WO | 2020223434 A1 | 11/2020 |

OTHER PUBLICATIONS

Wanyan, Tingyi, et al. "Contrastive learning improves critical event prediction in COVID-19 patients." Patterns 2.12 (2021). (Year: 2021).*

(Continued)

*Primary Examiner* — Devin C Hein
(74) *Attorney, Agent, or Firm* — W&G Law Group

(57) ABSTRACT

Disclosed is an system for predicting end-stage renal disease complication risk based on contrastive learning, including an end-stage renal disease data preparation module, configured to extract structured data of a patient by using a hospital electronic information system and daily monitoring equipment, and process the structured data to obtain augmented structured data; and a complication risk prediction module, configured to construct a complication representation learning model and a complication risk prediction model, perform training and learning on the augmented structured data through the complication representation learning model to obtain a complication representation, and perform end-stage renal disease complication risk prediction by using the complication representation through the complication risk prediction model.

7 Claims, 3 Drawing Sheets

(56) References Cited

OTHER PUBLICATIONS

W. A. Rivera, A. Goel and J. P. Kincaid, "OUPS: A Combined Approach Using SMOTE and Propensity Score Matching," 2014 13th International Conference on Machine Learning and Applications, Detroit, MI, USA, 2014, pp. 424-427, doi: 10.1109/ICMLA.2014.106. (Year: 2014).*
Zang C, Wang F. SCEHR: Supervised Contrastive Learning for Clinical Risk Prediction using Electronic Health Records. Proc IEEE Int Conf Data Min. Dec. 2021; 2021:857-866. doi: 10.1109/icdm51629.2021.00097. PMID: 36438203; PMCID: PMC9692209. (Year: 2021).*
Notice Of Allowance(CN202210838416.5); dated Sep. 9, 2022.
First Office Action(CN202210838416.5); dated Aug. 31, 2022.
Cox-regression-analysis-in-risk-factors-of-long-term-maintenance-he-modialysis-for-end-stage-renal-disease-patient.
Cardiac-Complication-Risk-Profiling-for-Cancer-Survivors-via-Multi-View-Multi-Task-Learning.

* cited by examiner

SYSTEM FOR PREDICTING END-STAGE RENAL DISEASE COMPLICATION RISK BASED ON CONTRASTIVE LEARNING

CROSS-REFERENCE TO RELATED APPLICATIONS

The present application claims priority to Chinese Patent Application No. 202210838416.5, filed on Jul. 18, 2022, the content of which is incorporated herein by reference in its entirety.

TECHNICAL FIELD

The present application relates to the technical field of medical health information, in particular to a system for predicting end-stage renal disease complication risk based on contrastive learning.

BACKGROUND

End-stage renal disease has a long course, and many complications may occur during the long-term treatment, including vascular infection, hypertension, coronary heart disease, insomnia, depression, etc., which seriously affects the quality of life of patients. Therefore, it is necessary to make risk prediction and early intervention for complications of end-stage renal disease. In the long-term treatment process, the hospital electronic information system has accumulated a large number of structured medical data over time, including multi-dimensional and multi-scale clinical features and various kinds of outcome event labels. Clinical data in real scenes are faced with the problems of complex structure, unbalanced positive and negative samples, and few samples in some categories, therefore, it is difficult to directly apply the existing machine learning methods to obtain effective prediction results. Nowadays, contrastive learning has been widely used in various fields, and the performance of the whole model can be improved by learning representation through contrastive learning framework, but it still faces some problems when applied to the risk prediction of complications of end-stage renal disease. On the one hand, traditional contrastive learning is prone to feature collapse. One disadvantage of self-supervised contrastive learning is that it is very easy to map all inputs to the same vector without the correction of positive and negative examples, thus causing feature collapse. Even if label data is introduced for supervised learning, although the embedding vectors will not completely collapse, they may still collapse along a specific dimension, which leads to the embedding vectors can only be effective in the subspace of the lower dimension. On the other hand, traditional contrastive learning is oriented to image data and text data, and the data augmentation methods thereof (such as image flipping, color changing, scaling and other operations) are not suitable for structured medical data.

Aiming to overcome the shortcomings of the prior art, and to solve the problems that the complicated data in the end-stage renal disease scene is difficult to be fused and the labels are not balanced and the like, this patent proposes a system for predicting end-stage renal disease complication risk based on contrastive learning, and constructs a system for predicting the end-stage renal disease complication risk, so as to provide accurate and effective decision support for clinical decision-making.

SUMMARY

The present application aims to provide a system for predicting an end-stage renal disease complication risk based on contrastive learning, which solve the problems that complex data in the end-stage renal disease scene are difficult to be fused and the labels are not balanced in the prior art.

The technical solution adopted by the present application is as follows:

an system for predicting end-stage renal disease complication risk based on contrastive learning includes:

an end-stage renal disease data preparation module, configured to extract structured data of a patient by using a hospital electronic information system and daily monitoring equipment, and process the structured data to obtain augmented structured data; and a complication risk prediction module, configured to construct a complication representation learning model and a complication risk prediction model, and perform training and learning on the augmented structured data through the complication representation learning model to obtain a complication representation, and perform end-stage renal disease complication risk prediction by using the complication representation through the complication risk prediction model.

Further, the end-stage renal disease data preparation module specifically includes:

a data acquisition unit, configured to extract the structured data by using the hospital electronic information system and the daily monitoring equipment;

a data cleaning unit, configured to perform missing value processing, error value detecting, duplicated data eliminating and/or inconsistency eliminating operations on the structured data, to obtain static data, one-dimensional time series data and two-dimensional time series data;

a data fusion unit, configured to splice one-dimensional packed data and the static data obtained by performing one-dimensional convolution and two-dimensional convolution operations respectively on the one-dimensional time series data and the two-dimensional time series data to obtain an original fusion feature; and a data augmentation unit, configured to obtain the augmented structured data by adopting the data augmentation method combining propensity score matching with Synthetic Minority Oversampling Technique (SMOTE) for the original fusion feature.

Further, the structured data comprise demographic data, surgical data, medication data, chemical test data, diagnostic data and daily monitoring data.

Further, the data augmentation unit specifically includes:

a fusion feature component, configured to take a patient with an end-stage renal disease complication as a positive sample, take a patient with no the end-stage renal disease complication as a negative sample, represent the positive sample and the negative sample with the original fusion features, and perform normalization operation on the original fusion features of the positive sample and the negative sample, to obtain a fusion feature; a propensity score component, configured to select one dimension of the fusion feature arbitrarily to serve as an intervening variable, with other dimensions of the fusion feature serving as a concomitant variable set, to obtain a propensity score through loss function optimization;

a matching component, configured to make all the positive samples constitute a positive sample universal set, make all the negative samples constitute a negative sample universal set, and make the positive sample universal set match negative sample subsets in the negative sample universal set based on the propensity score;

a positive sample augmentation component, configured to obtain an augmented positive sample by performing a SMOTE algorithm on the positive sample universal set, the positive sample universal set and the augmented positive sample constituting a positive sample augmented set;

a negative sample augmentation component, configured to obtain an augmented negative sample by performing a SMOTE algorithm on the negative sample subsets, the negative sample subsets and the augmented negative sample constituting a negative sample augmented set; and an augmentation component, configured to make the positive sample augmented set and the negative sample augmented set constitute jointly the augmented structured data.

Further, the complication risk prediction module specifically includes:

a complication representation learning model constructing unit, configured to construct a complication representation learning model;

a complication risk prediction model constructing unit, configured to construct a complication risk prediction model;

a complication representation learning unit, configured to perform training and learning on the augmented structured data through the complication representation learning model to obtain a complication representation; and a risk prediction unit, configured to perform end-stage renal disease complication risk prediction on the complication representation through the complication risk prediction model.

Further, the complication representation learning model constructing unit specifically includes:

a complication representation learning model defining component, configured to construct a network structure and a total loss function; and a complication representation learning model optimizing component, configured to optimize parameters in the network structure through a gradient descent method, so that the total loss function reaches convergence, and constructing of the complication representation learning model is completed.

Further, the complication representation learning model defining component specifically includes:

a parameter definition block, configured to define hyperparameters of the network structure, and comprising an encoder and a projector;

a feature normalization block, configured to input the augmented structured data in pairs into the encoder, to obtain the initial complication representation, obtain the contrastive representation from the initial complication representation through the projector, and obtaining the normalization representation from the contrastive representation through feature normalization operation; and a total loss definition block, configured to construct the total loss function by using the normalization representation, a covariance item, a variance item, a category similarity measure item and an augmented similarity measure item.

Further, the complication risk prediction model constructing unit specifically includes:

a complication risk prediction model defining component, configured to define a network structure of an end-stage renal disease complication risk prediction network, and select an activation function and a loss function of the end-stage renal disease complication risk prediction network and an optimization method; and a complication risk prediction model optimizing component, configured to train the complication risk prediction network by using the optimization method, to complete constructing of the complication risk prediction model.

The present application has the beneficial effects that:

1. A method of data augmentation and positive and negative sample matching based on propensity score is proposed to augment structured end-stage renal disease data and solve the problem of imbalance between positive and negative samples.
2. A hierarchical contrast learning framework is proposed, aiming at the similarity comparison of augmented data, data of the same category and data of different categories at different levels, and a contrastive loss function is constructed by using covariance terms, variance terms, category similarity measures and augmented similarity measures, so as to prevent feature collapse from multiple angles from a more comprehensive perspective and obtain a good representation effect, thus improving the model performance.
3. The traditional propensity score matching method can only handle binary variables, and the present application improves the loss optimization method of propensity score, so that it can handle variables with continuous values.

DESCRIPTION OF EMBODIMENTS

The following description of at least one exemplary embodiment is merely illustrative in nature and is in no way intended to limit the present application, its application or uses. Based on the embodiments in the present application, all other embodiments obtained by those skilled in the art without creative work belong to the scope of protection of the present application.

Figure 1:
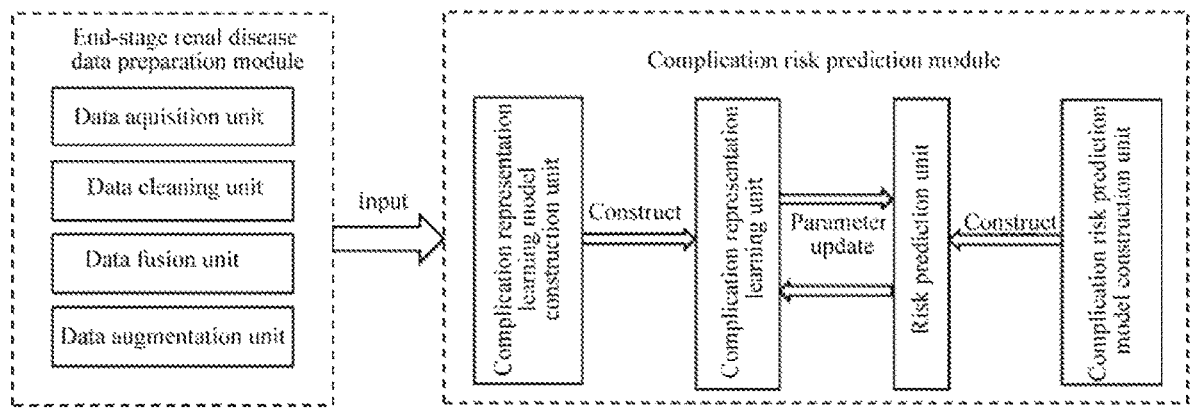
FIG. 1 is a schematic diagram of an system for predicting end-stage renal disease complication risk based on contrastive learning.

See FIG. 1.

An system for predicting end-stage renal disease complication risk based on contrastive learning includes:

an end-stage renal disease data preparation module, configured to extract structured data of a patient by using a hospital electronic information system and daily monitoring equipment, and process the structured data to obtain augmented structured data; and a complication risk prediction module, configured to construct a complication representation learning model and a complication risk prediction model, and perform training and learning on the augmented structured data through the complication representation learning model to obtain a complication representation, and perform end-stage renal disease complication risk prediction by using the complication representation through the complication risk prediction model.

The end-stage renal disease data preparation module specifically includes:
- a data acquisition unit, configured to extract the structured data by using the hospital electronic information system and the daily monitoring equipment;
- a data cleaning unit, configured to perform missing value processing, error value detecting, duplicated data eliminating and/or inconsistency eliminating operations on the structured data, to obtain static data, one-dimensional time series data and two-dimensional time series data;
- a data fusion unit, configured to splice one-dimensional packed data and the static data obtained by performing one-dimensional convolution and two-dimensional convolution operations respectively on the one-dimensional time series data and the two-dimensional time series data to obtain an original fusion feature; and
- a data augmentation unit, configured to obtain the augmented structured data by adopting the data augmentation method combining propensity score matching with SMOTE for the original fusion feature.

The structured data comprise demographic data, surgical data, medication data, chemical test data, diagnostic data and daily monitoring data.

The data augmentation unit specifically includes:
- a fusion feature component, configured to take a patient with an end-stage renal disease complication as a positive sample, take a patient with no the end-stage renal disease complication as a negative sample, represent the positive sample and the negative sample with the original fusion features, and perform normalization operation on the original fusion features of the positive sample and the negative sample, to obtain a fusion feature;
- a propensity score component, configured to select one dimension of the fusion feature arbitrarily to serve as an intervening variable, with other dimensions of the fusion feature serving as a concomitant variable set, to obtain a propensity score through loss function optimization;
- a matching component, configured to make all the positive samples constitute a positive sample universal set, make all the negative samples constitute a negative sample universal set, and make the positive sample universal set match negative sample subsets in the negative sample universal set based on the propensity score;
- a positive sample augmentation component, configured to obtain an augmented positive sample by performing a SMOTE algorithm on the positive sample universal set, the positive sample universal set and the augmented positive sample constituting a positive sample augmented set;
- a negative sample augmentation component, configured to obtain an augmented negative sample by performing a SMOTE algorithm on the negative sample subsets, the negative sample subsets and the augmented negative sample constituting a negative sample augmented set; and
- an augmentation component, configured to make the positive sample augmented set and the negative sample augmented set constitute jointly the augmented structured data.

The complication risk prediction module specifically includes:
- a complication representation learning model constructing unit, configured to construct a complication representation learning model;
- a complication risk prediction model constructing unit, configured to construct a complication risk prediction model;
- a complication representation learning unit, configured to perform training and learning on the augmented structured data through the complication representation learning model to obtain a complication representation; and
- a risk prediction unit, configured to perform end-stage renal disease complication risk prediction on the complication representation through the complication risk prediction model.

Further, the complication representation learning model constructing unit specifically includes:
- a complication representation learning model defining component, configured to construct a network structure and a total loss function; and
- a complication representation learning model optimizing component, configured to optimize parameters in the network structure through a gradient descent method, so that the total loss function reaches convergence, and constructing of the complication representation learning model is completed.

The complication representation learning model defining component specifically includes:
- a parameter definition block, configured to define hyperparameters of the network structure, and comprising an encoder and a projector;
- a feature normalization block, configured to input the augmented structured data in pairs into the encoder, to obtain the initial complication representation, obtain the contrastive representation from the initial complication representation through the projector, and obtaining the normalization representation from the contrastive representation through feature normalization operation; and
- a total loss definition block, configured to construct the total loss function by using the normalization representation, a covariance item, a variance item, a category similarity measure item and an augmented similarity measure item.

The complication risk prediction model constructing unit specifically includes:
- a complication risk prediction model defining component, configured to define a network structure of an end-stage renal disease complication risk prediction network, and select an activation function and a loss function of the end-stage renal disease complication risk prediction network and an optimization method; and
- a complication risk prediction model optimizing component, configured to train the complication risk prediction network by using the optimization method, to complete constructing of the complication risk prediction model.

Figure 2:
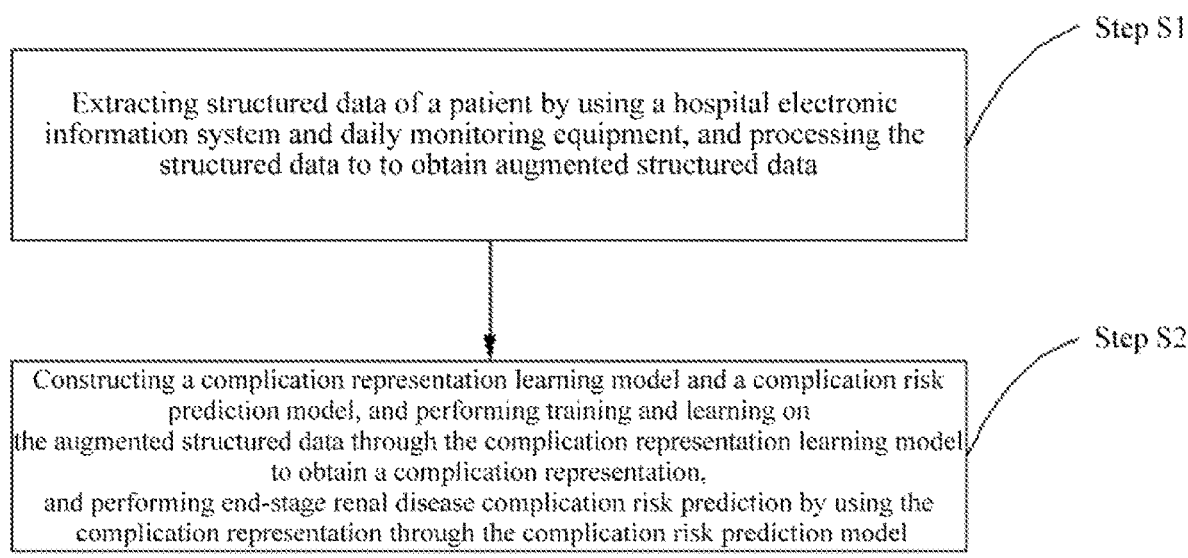
FIG. 2 is a flowchart of an end-stage renal disease complication risk prediction method based on contrastive learning.

See FIG. 2

An end-stage renal disease complication risk prediction method based on contrastive learning includes the following steps:

S1, extracting structured data of a patient by using a hospital electronic information system and daily monitoring equipment, and processing the structured data to obtain augmented structured data; and S2, constructing a complication representation learning model and a complication risk prediction model, and performing training and learning on the augmented structured data through the complication representation learning model to obtain a complication representation, and performing end-stage renal disease complication risk prediction by using the complication representation through the complication risk prediction model.

EXAMPLES

Figure 3:
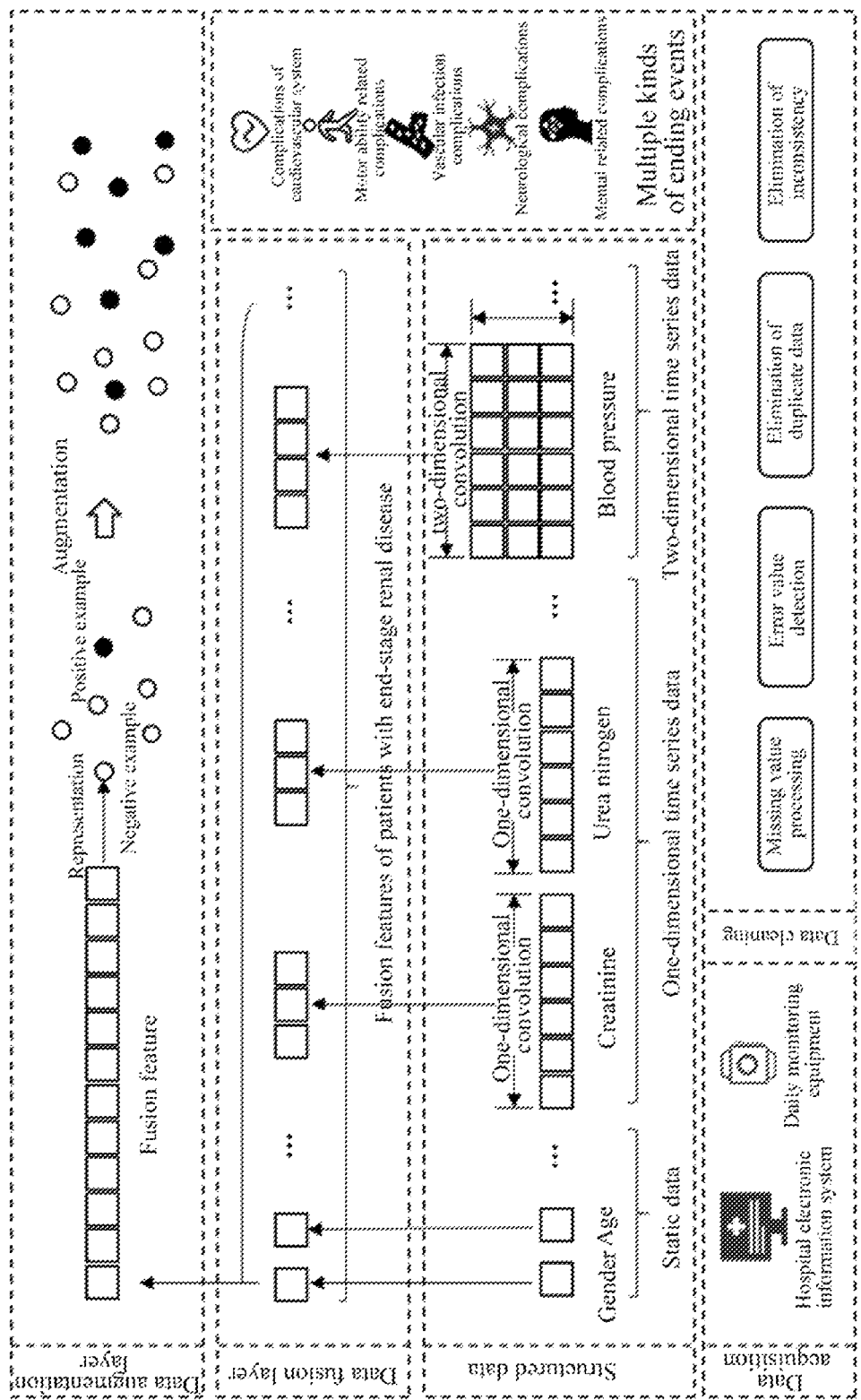
FIG. 3 is a schematic diagram of an end-stage renal disease data preparation module according to an embodiment of the present application.

See FIG. 3, an end-stage renal disease data preparation module extracts structured data of a patient by using a hospital electronic information system and daily monitoring equipment, and processes the structured data to obtain augmented structured data.

A data acquisition unit extracts structured data by using a hospital electronic information system and daily monitoring equipment; the structured data includes demographic data, surgical data, medication data, laboratory data, diagnostic data and daily monitoring data; demographic data: gender, age, nationality and region; Surgical data: mainly vascular access surgical information; drug use data: dialysis plan, drug use for complications, etc.; test data: creatinine, urea nitrogen, etc.; diagnostic data: complications; daily monitoring data: blood pressure, weight, etc.

A data cleaning unit performs missing value processing, error value detection, duplicate data elimination and/or inconsistency elimination operations on the structured data to obtain static data, one-dimensional time series data and two-dimensional time series data; the data cleaning unit mainly screens out the dirty data that is not reasonable; taking blood pressure data as an example, firstly, blood pressure data containing special characters are filtered out; secondly, the data of systolic blood pressure exceeding 250 mmHg or less than are screened out.

A data fusion unit splices one-dimensional packed data and the static data obtained by performing one-dimensional convolution and two-dimensional convolution operations respectively on the one-dimensional time series data and the two-dimensional time series data to obtain an original fusion feature;

the data fusion unit mainly integrates the features of multi-dimensional and multi-scale clinical structured data, and organizes it into a unified structure, which is convenient for subsequent methods; structured data mainly include static data such as gender and age, one-dimensional time series data such as creatinine and urea nitrogen, and two-dimensional time series data such as blood pressure (two time dimensions: namely, during a single hemodialysis process and between multiple hemodialysis processes).

A data augmentation unit is used to augment the original fusion features by a data augmentation method combining propensity score matching with SMOTE to obtain augmented structured data; the data augmentation unit is mainly used to increase the diversity of samples and solve the problem of unbalanced positive and negative samples. The present application adopts a data augmentation method combining propensity score matching with SMOTE to augment structured end-stage renal disease data and solve the problem of unbalanced positive and negative samples.

A fusion feature component is used to take a patient with an end-stage renal disease complication as a positive sample, take a patient with no the end-stage renal disease complication as a negative sample, represent the positive sample and the negative sample with the original fusion features, and perform normalization operation on the original fusion features of the positive sample and the negative sample, to obtain a fusion feature. In this embodiment, patients with cardiovascular complications are used as positive samples and patients without cardiovascular complications are used as negative samples.

0-1 normalization operation is carried out on the positive samples and the negative samples, and the fusion features of the normalized sample x is $$x^2, \ldots, x^m), x^m = \frac{x_{ori}^m - \min(x_{ori}^m)}{\max(x_{ori}^m) - \min(x_{ori}^m)}$$

where, $x_{ori}^m$ represents the original fusion feature of the m dimension, $\min(x_{ori}^m)$ represents the minimum value of the original fusion feature of the m dimension, and $\max(x_{ori}^m)$ represents the maximum value of the original fusion feature of the m dimension.

A propensity score component is used to select one dimension of the fusion feature arbitrarily to serve as an intervening variable, with other dimensions of the fusion feature serving as a concomitant variable set, to obtain a propensity score through loss function optimization.

Any one dimension $x^v$ (v=1, 2, . . . , m) of the fusion feature x is selected as the intervention variable, and the other dimensions $\widetilde{x^v} = (x^1, \ldots, x^{v-1}, x^{v+1}, \ldots, x^m)$ as the covariate set to fit $x^v$ with $\widetilde{x^v}$, that is, $$a^v(x) = \frac{1}{1 + e^{\beta_0^v - \beta^v x^{\widetilde{v}}}}$$

is taken as the propensity score of the intervention variable $x^v$.

The parameters $\beta_0^v, \beta^v$ are optimized by a loss function $$L(a^v, x^v) = \sum_{i=1}^{n} \log(\cosh(a_i^v - x_i^v)) + \|\beta^v\|_1,$$

and the optimization method can be a gradient descent adam method. where $\|\cdot\|_1$ represents a $L_1$ norm, n is the total sample size, $x_i^v$ is the $v^{th}$ variable of the $i^{th}$ sample, and $a_i^v$ is the propensity score of $x_i^v$, that is $a_i^v = a^v(x_i)$.

A matching component is used to make all the positive samples constitute a positive sample universal set, make all the negative samples constitute a negative sample universal set, and make the positive sample universal set match negative sample subsets in the negative sample universal set based on the propensity score.

All the positive samples constitute a universal set of positive samples, which is record as $\{x_t\}$; all the negative samples constitute a universal set of negative samples, which is recorded as $\{x_f\}$. Any positive sample $x_p \in \{x_t\}$ is selected, and the fusion feature of the positive sample $x_p$ is expressed as $(x_p^1, x_p^2, \ldots, x_p^m)$. If any feature b is selected as the intervention variable $x_p^b$ of the positive sample $x_p$, the propensity score of the positive sample $x_p$ is $a_p^b = a^b(x_p)$, and a suitable negative sample $x_q$ is matched based on the propensity score, and the fusion feature of the negative sample $x_q$ is expressed as $(x_q^1, x_q^2, \ldots, x_q^m)$ so that $\mathrm{argmin}_{x_q} |a_q^b - a_p^b|$, where $a_q^b = a^b(x_q)$, $x_q \in \{x_f\}$. Based on the above matching method, the negative sample subset $\{x_e\} \in \{x_f\}$ matched with the universal set $\{x_t\}$ of positive samples is selected for matching.

A positive sample augmentation component is used to obtain an augmented positive sample by performing a SMOTE algorithm on the positive sample universal set, the positive sample universal set and the augmented positive sample constituting a positive sample augmented set.

u similar samples $x_{p1}$, $x_{p2}$, ... which has the smallest Mahalanobis distance d from the positive sample $x_p$ are selected from the universal set $\{x_t\}$ of positive samples. The Mahalanobis distance between samples $x_p$ and $x_{pu}$ $d(x_p, x_{pu}) = \sqrt{(x_p - x_{pu})^T C_p^{-1} (x_p - x_{pu})}$, where $C_p$ is a covariance matrix, $C_p = \mathrm{cov}(x_p, x_{pu})$. u augmented positive samples $\hat{x}_{p1}, \hat{x}_{p2}, \ldots, \hat{x}_{pu}$, are obtained based on SMOTE algorithm. The fusion feature of the augmented positive sample $\hat{x}_{iu}$ is expressed as $$(\hat{x}_{pu}^1, \hat{x}_{pu}^2, \ldots, \hat{x}_{pu}^m), \text{ where } \hat{x}_{pu}^m = \frac{1}{2}(x_{pu}^m + x_p^m).$$

The universal set $\{x_t\}$ of positive samples and its augmented positive samples constitute the positive sample augmentation set.

A negative sample augmentation component is used to obtain an augmented negative sample by performing a SMOTE algorithm on the negative sample subsets, the negative sample subsets and the augmented negative sample constituting a negative sample augmented set.

A negative sample $x_q \in$ a negative sample subset $\{x_e\}$, and u similar negative samples $x_{q1}, x_{q2}, \ldots, x_{qu}$ which has the smallest Mahalanobis distance d from the negative sample $x_q$ are selected from the universal set of negative samples $\{x_f\}$. The Mahalanobis distance between negative samples $x_q$ and $x_{qu}$ $d(x_q, x_{qu}) = \sqrt{(x_q - x_{qu})^T C_q^{-1} (x_q - x_{qu})}$, where $C_q$ is a covariance matrix, $C_q = \mathrm{cov}(x_q, x_{qu})$. u augmented negative samples $\hat{x}_{q1}, \hat{x}_{q2}, \ldots, \hat{x}_{qu}$ are obtained based on SMOTE algorithm. The fusion feature of the augmented negative sample $\hat{x}_{qu}$ is expressed as $(\hat{x}_{qu}^1, \hat{x}_{qu}^2, \ldots, \hat{x}_{qu}^m)$, where $$\hat{x}_{qu}^m = \frac{1}{2}(x_{qu}^m + x_q^m).$$

A negative sample subset $\{x_e\}$ and its augmented negative samples constitute a negative sample augmentation set.

An augmentation component is used to make the positive sample augmented set and the negative sample augmented set constitute jointly the augmented structured data.

Figure 4:
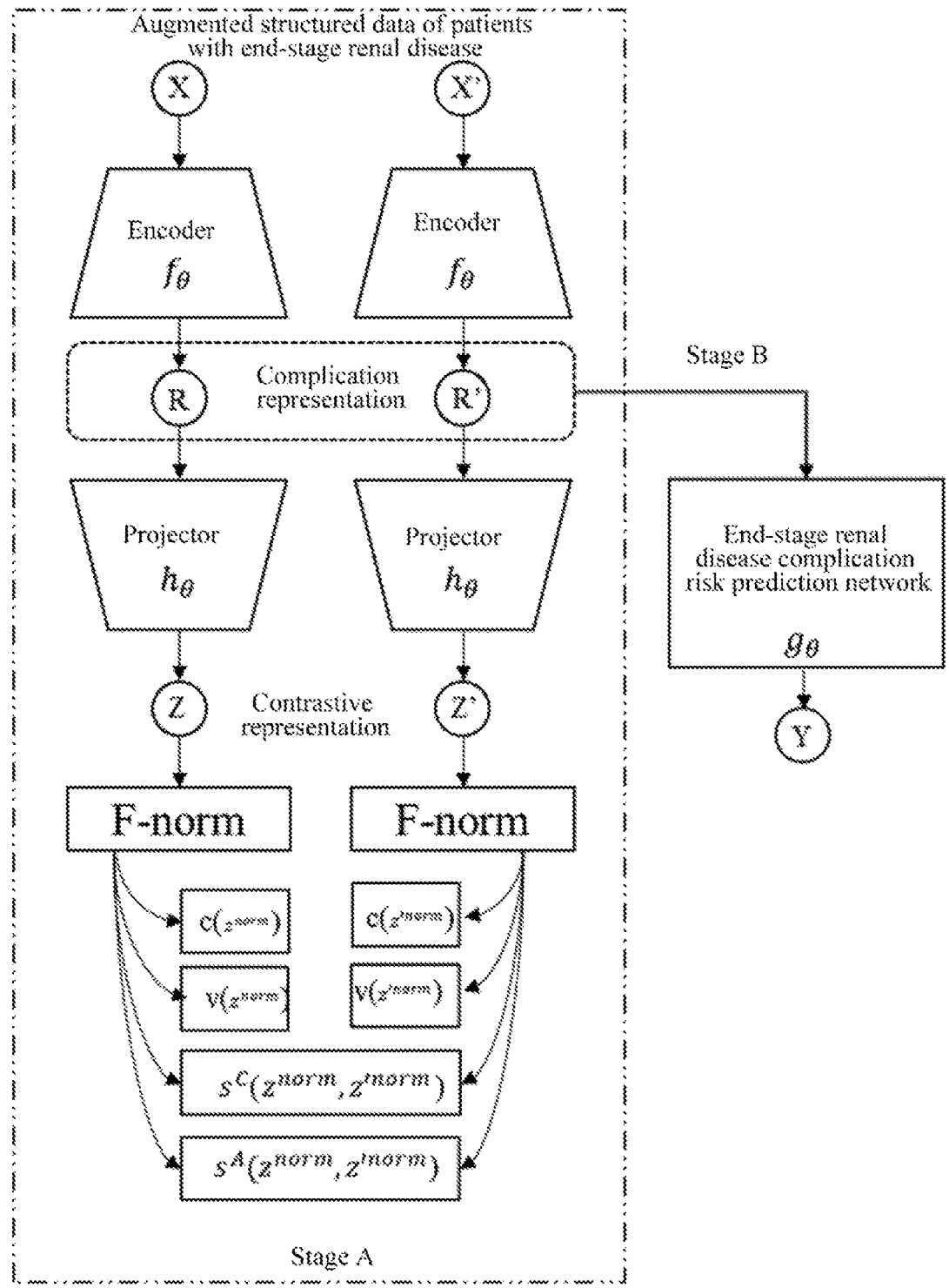
FIG. 4 is a schematic diagram of a complication risk prediction module according to an embodiment of the present application.

See FIG. 4, complication risk prediction module, configured to construct a complication representation learning model and a complication risk prediction model, and perform training and learning on the augmented structured data through the complication representation learning model to obtain a complication representation, and perform end-stage renal disease complication risk prediction by using the complication representation through the complication risk prediction model.

A complication representation learning model constructing unit is used to construct a complication representation learning model;

a complication representation learning model defining component is used to construct a network structure and a total loss function;

a parameter definition block is used to define hyper-parameters of the network structure, and comprises an encoder $f_\theta$ and a projector $h_\theta$;

The encoder is a five-layer fully connected network with 1024, 512, 256, 128 and 64 nodes, and the activation function is relu. The projector $h_\theta$ is a three-layer attention network with 64,128,256 nodes and the activation function is relu;

A feature normalization block is used to input the augmented structured data in pairs into the encoder $f_\theta$, to obtain the initial complication representation, obtain the contrastive representation from the initial complication representation through the projector $h_\theta$, and obtaining the normalization representation from the contrastive representation through feature normalization operation.

The augmented structured data (X,X') is input into the encoder $f_\theta$ in pairs, and the initial complication representation (R,R') is obtained. A contrastive representation (Z,Z') is obtained from the initial complication representation through the projector $h_\theta$, and a normalization representation $$Z_{norm} = \frac{Z - \mu_Z}{\sigma_Z}$$

is obtained from the contrastive representation through the feature normalization operation F-norm, where $\mu_Z$ is an average value of the z feature dimensions of the contrastive representation and $\sigma_Z$ is a standard deviation of the z feature dimensions of the contrastive representation.

A total loss definition block is used to construct the total loss function by using the normalization representation, a covariance item, a variance item, a category similarity measure item and an augmented similarity measure item.

In order to prevent feature collapse, a total loss function is constructed by using covariance terms $c(Z^{norm})$ and $c(Z'^{norm})$, variance $v(Z^{norm})$ and $v(Z'^{norm})$, category similarity measure term $s^c(Z^{norm}, Z'^{norm})$ and augmented similarity measure term $s^A(Z^{norm}, Z'^{norm})$:

$$L = \sum_i^{2(u+1)N} L_i$$

$$L_i = \lambda s_i + \mu v_i + v c_i$$

$$s_i = s^C(Z_i^{norm}, Z_i'^{norm}) + s^A(Z_i^{norm}, Z_i'^{norm})$$

$$v_i = v(Z_i^{norm}) + v(Z_i'^{norm})$$

$$c_i = c(Z_i^{norm}) + c(Z_i'^{norm})$$

where N is the positive sample size of a batch randomly sampled, and since each positive sample matches a negative sample and u samples are augmented respectively, $2(u+1)N$ is the sample size of an augmented batch, including augmented samples, samples of the same category and samples of different categories. $2(u+1)N$ samples are randomly sampled in pairs to constitute the paired augmented structured data (X, X') described above. In present application, $v=1$, $\lambda=\mu>1$. The optimal solution is obtained by grid search by taking $\lambda$, $\mu$ as hyper-parameters.

Among them, the category similarity measure item measures the category similarity of the whole batch of samples input in pairs. The specific formula is $$s^C(Z^{norm}, Z'^{norm}) =$$

$$\frac{-1}{2(u+1)N} \sum_{j}^{2(u+1)N} 1_{i \ne j} 1_{y_i = y_j} \log \frac{E_{ij}}{\sum_{k}^{2(u+1)N} 1_{i \ne k} 1_{y_i \ne y_k} E_{ik}}$$

$$E_{ij} = \frac{z_i^{norm} \cdot z_j^{norm}}{\|z_i^{norm}\| \cdot \|z_j^{norm}\|}$$

where $\|Z_i^{norm}\|$ represents a norm of a vector $Z_i^{norm}$, $\|Z_j^{norm}\|$ represents a norm of a vector $Z_j^{norm}$, $E_{ij}$ represents a cosine distance between the sample i and the sample j, and $E_{ik}$ represents a cosine distance between the sample i and the sample k. $1_{i \ne j}$ is 1 only if i≠j, otherwise 0. $y_i$ is the category label of a sample i, $y_i$=1 means that the patient with end-stage renal disease has cardiovascular complications, $y_i$=0 means that the patient with end-stage renal disease has no cardiovascular complications. This s similar for $y_k$, $y_i=y_j$ means that samples i and j belong to the same category. $1_{y_i=y_j}$ is 1 only if $y_i=y_j$, otherwise 0; $1_{i \ne k}$ is 1 only if i≠k, otherwise 0; $1_{y_i \ne y_k}$ is 1 only if $y_i \ne y_k$, otherwise 0. Taking $s^C(Z^{norm}, Z'^{norm})$ as a loss term, the cosine similarity of the same category of samples (numerators in the formula, $1_{i \ne j}$, $1_{y_i=y_j}$) is constrained to be as large as possible, and the cosine similarity of different categories of samples (denominators in the formula, $1_{i \ne k}$, $1_{y_i \ne y_k}$) is as small as possible.

A computational formula of the augmented similarity measure item $s^A(Z^{norm}, Z'^{norm})$ is $$s^A(Z^{norm}, Z'^{norm}) =$$

$$\frac{-1}{2(u+1)N} \sum_{j}^{2(u+1)N} 1_{i \ne j} 1_{A_i = A_j} \log \frac{E_{ij}}{\sum_{k}^{2(u+1)N} 1_{i \ne k} 1_{A_i \ne A_k} E_{ik}}$$

where $A_i$ represents an augmented label of the sample i, $A_i=A_j$ represents that the sample i and the sample j are obtained by augmenting the same sample, and $A_i \ne A_k$ represents that the sample i and the sample j are obtained by augmenting different samples. Taking $s^A(Z^{norm}, Z'^{norm})$ as a loss term, the cosine similarity of augmented samples (numerators in the formula ($1_{i \ne j}$, $1_{A_i=A_j}$) is constrained to be as large as possible, and the cosine similarity of non-augmented samples (denominators in the formula, $1_{i \ne k}$, $1_{A_i \ne A_k}$) is as small as possible. According to the present application, the category similarity measurement item $s^C$ and the augmented similarity measurement item $s^A$ are combined, so that the samples of the same category are as close as possible in the characterization space, and the samples of different categories are as far away as possible in the characterization space; on this basis, the augmented samples are further close in the characterization space, and the non-augmented samples are far away in the characterization space, thereby achieving the purpose of reducing feature collapse.

The specific formula of the variance item $v(Z^{norm})$ is $$v(Z^{norm}) = \frac{1}{m} \sum_{j}^{m} \max\left(0, 1 - \sqrt{\text{Var}(Z^{norm^j}) + 0.000001}\right)$$

where m is the dimension of $Z^{norm}$, $Z^{norm^j}$ represents the feature of the $j^{th}$ dimension of $Z^{norm}$, and Var represents a variance operator, $\text{Var}(Z^{norm^j})$ represents the variance of the $j^{th}$ dimension of $Z^{norm}$. The prototype of the above formula is hing-loss, which makes the variance of $Z^{norm}$ in each dimension push to 1, so that $Z^{norm}$ will not collapse to a single value in each dimension. It is the same for ($Z'^{norm}$).

The detailed formula of the covariance term $c(Z^{norm})$ is:

$$c(Z^{norm}) = \frac{1}{2(u+1)N - 1} \sum_{i \ne j}$$

$$\left(Z^{norm^i} - \frac{1}{2(u+1)N} \sum_{i}^{2(u+1)N} Z^{norm^i}\right)\left(Z^{norm^j} - \frac{1}{2(u+1)N} \sum_{j}^{2(u+1)N} Z^{norm^j}\right)^T$$

The above formula represents the sum of covariances of $Z^{norm}$ between different dimensions. As a loss term, the above formula makes the redundant information of $Z^{norm}$ between different dimensions as little as possible. In other words, the above formula makes different dimensions of $Z^{norm}$ as different as possible, thus reducing the occurrence of feature collapse.

A complication representation learning model optimizing component is used to optimize parameters in the network structure through a gradient descent method, so that the total loss function reaches convergence, and constructing of the complication representation learning model is completed.

The encoder $f_\theta$ and projector $h_\theta$ are trained by comparing the total loss function L, the goal (taking predicting cardiovascular complications as an example) is to obtain the contrastive representation of cardiovascular complications in patients with end-stage renal disease, so that the representations of the same class are close, the representations of different classes are far away, the representations of augmented samples are close, and the representations of non-augmented samples are far away. The optimization method can be gradient descent adam method and the like.

A complication risk prediction model constructing unit is used to construct a complication risk prediction model;
  a complication risk prediction model defining component is used to define a network structure of an end-stage renal disease complication risk prediction network, and select an activation function and a loss function of the end-stage renal disease complication risk prediction network and an optimization method;
  a complication risk prediction model optimizing component is used to train the complication risk prediction network by using the optimization method, to complete constructing of the complication risk prediction model.

Firstly, a three-layer fully connected network is defined as the network structure of the end-stage renal disease complication risk prediction network $g_\theta$, and the number of nodes in the network structure of the end-stage renal disease complication risk prediction network $g_\theta$ is 16, 4 and 1 in turn.

Relu is selected as the activation function of the full connection layer of the end-stage renal disease complication risk prediction network $g_\theta$, sigmoid as the activation function of the output layer, the cross entropy loss function as the loss function, and adam as the optimization method; the optimization method adam method is used to train the weight parameters of the complication risk prediction network to complete the construction of the complication risk prediction model.

When the total loss L converges, the weight parameters of the encoder $f_\theta$ are frozen to train the weight parameters of the end-stage renal disease complication risk prediction network $g_\theta$.

A complication representation learning unit is used to perform training and learning on the augmented structured data through the complication representation learning model to obtain a complication representation; and a risk prediction unit is used to perform end-stage renal disease complication risk prediction on the complication representation through the complication risk prediction model.

Taking the prediction of cardiovascular complications of end-stage renal disease as an example, the samples are input into the model in batches. A batch of samples contains N positive samples (with cardiovascular complications) and uN augmented positive samples, as well as matched N negative samples and uN augmented negative samples, totaling 2N(u+1) samples. The label y=1 indicates that cardiovascular complications occur, and y=0 indicates that cardiovascular complications do not occur. The output is the probability of cardiovascular complications in patients with end-stage renal disease.

In this application, the term "controller" and/or "module" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a Field Programmable Gate Array (FPGA); a processor circuit (shared, dedicated, or group) that executes code; a memory circuit (shared, dedicated, or group) that stores code executed by the processor circuit; other suitable hardware components (e.g., op amp circuit integrator as part of the heat flux data module) that provide the described functionality; or a combination of some or all of the above, such as in a system-on-chip.

The term memory is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general-purpose computer to execute one or more particular functions embodied in computer programs. The functional blocks, flowchart components, and other elements described above serve as software specifications, which can be translated into the computer programs by the routine work of a skilled technician or programmer.

What has been described above is only the preferred embodiment of the present application, and it is not used to limit the present application. For those skilled in the art, the present application may have various modifications and changes. Any modification, equivalent substitution, improvement, etc. made within the spirit and principle of the present application shall be included in the protection scope of the present application.

What is claimed is:

1. A system for predicting end-stage renal disease complication risk based on contrastive learning, comprising:

an end-stage renal disease data preparation module, configured to extract structured data of a patient using a hospital electronic information system and daily monitoring equipment, and process the structured data to obtain augmented structured data;

the end-stage renal disease data preparation module comprising:

a data augmentation unit, configured to obtain the augmented structured data using a data augmentation method combining propensity score matching with Synthetic Minority Oversampling Technique (SMOTE) for original fusion features obtained by processing the structured data;

the data augmentation unit comprising:

a fusion feature component, configured to take a patient with an end-stage renal disease complication as a positive sample, take a patient with no the end-stage renal disease complication as a negative sample, represent the positive sample and the negative sample with the original fusion features, and perform normalization operation on the original fusion features of the positive sample and the negative sample, to obtain a fusion feature;

a propensity score component, configured to select one dimension of the fusion feature arbitrarily to serve as an intervening variable, with other dimensions of the fusion feature serving as a concomitant variable set, to obtain a propensity score through loss function optimization;

a matching component, configured to make all positive samples constitute a positive sample universal set, make all negative samples constitute a negative sample universal set, and make the positive sample universal set match negative sample subsets in the negative sample universal set based on the propensity score;

a positive sample augmentation component, configured to obtain an augmented positive sample by performing a SMOTE algorithm on the positive sample universal set, wherein the positive sample universal set and the augmented positive sample constitutes a positive sample augmented set;

a negative sample augmentation component, configured to obtain an augmented negative sample by performing a SMOTE algorithm on the negative sample subsets, wherein the negative sample subsets and the augmented negative sample constitutes a negative sample augmented set; and an augmentation component, configured to make the positive sample augmented set and the negative sample augmented set jointly constitute the augmented structured data; and a complication risk prediction module, configured to construct a complication representation learning model and a complication risk prediction model, and perform training and learning on the augmented structured data through the complication representation learning model to obtain a complication representation, and perform end-stage renal disease complication risk prediction using the complication representation through the complication risk prediction model;

wherein parameter construction of a total loss function of the complication representation learning model comprises a normalization representation, and a determining mode of the normalization representation comprises: inputting the augmented structured data in pairs into an encoder of the complication representation learning model, to obtain an initial complication representation, obtaining a contrastive representation from the initial complication representation through a projector of the complication representation learning model, and obtaining the normalization representation from the contrastive representation through feature normalization operation.

2. The system for predicting end-stage renal disease complication risk based on contrastive learning according to claim 1, wherein the end-stage renal disease data preparation module comprises:
a data acquisition unit, configured to extract the structured data using the hospital electronic information system and the daily monitoring equipment;
a data cleaning unit, configured to perform missing value processing, error value detecting, duplicated data eliminating and/or inconsistency eliminating operations on the structured data, to obtain static data, one-dimensional time series data and two-dimensional time series data;
a data fusion unit, configured to splice one-dimensional packed data and the static data obtained by performing one-dimensional convolution and two-dimensional convolution operations respectively on the one-dimensional time series data and the two-dimensional time series data, to obtain an original fusion feature; and
the data augmentation unit, configured to obtain the augmented structured data by adopting the data augmentation method combining propensity score matching with SMOTE for the original fusion feature.

3. The system for predicting end-stage renal disease complication risk based on contrastive learning according to claim 1, wherein the structured data comprise demographic data, surgical data, medication data, chemical test data, diagnostic data and daily monitoring data.

4. The system for predicting end-stage renal disease complication risk based on contrastive learning according to claim 1, wherein the complication risk prediction module specifically comprises:
a complication representation learning model constructing unit, configured to construct a complication representation learning model;
a complication risk prediction model constructing unit, configured to construct a complication risk prediction model;
a complication representation learning unit, configured to perform training and learning on the augmented structured data through the complication representation learning model to obtain a complication representation; and
a risk prediction unit, configured to perform end-stage renal disease complication risk prediction on the complication representation through the complication risk prediction model.

5. The system for predicting end-stage renal disease complication risk based on contrastive learning according to claim 4, wherein the complication representation learning model constructing unit specifically comprises:
a complication representation learning model defining component, configured to construct a network structure and a total loss function; and
a complication representation learning model optimizing component, configured to optimize parameters in the network structure through a gradient descent method, so that the total loss function reaches convergence, and constructing of the complication representation learning model is completed.

6. The system for predicting end-stage renal disease complication risk based on contrastive learning according to claim 5, wherein the complication representation learning model defining component comprises:
a parameter definition block, configured to define hyperparameters of the network structure, wherein the parameter definition block comprises an encoder and a projector;
a feature normalization block, configured to input the augmented structured data in pairs into the encoder, to obtain the initial complication representation, obtain the contrastive representation from the initial complication representation through the projector, and obtaining the normalization representation from the contrastive representation through feature normalization operation; and
a total loss definition block, configured to construct the total loss function using the normalization representation, a covariance item, a variance item, a category similarity measure item and an augmented similarity measure item;
wherein the category similarity measure item is calculated as follows:

$$s^C(Z^{norm}, Z'^{norm}) = \frac{-1}{2(u+1)N} \sum_{j}^{2(u+1)N} 1_{i \ne j} 1_{y_i = y_j} \log \frac{E_{ij}}{\sum_{k}^{2(u+1)N} 1_{i \ne k} 1_{y_i \ne y_k} E_{ik}} E_{ij} = \frac{Z_i^{norm} \cdot Z_j^{norm}}{\|Z_i^{norm}\| \cdot \|Z_j^{norm}\|}$$

where $Z^{norm}$ represents the normalization representation, N represents a positive sample size of a batch randomly sampled, u represents the number of samples augmented respectively by each positive sample matching one negative sample, $2(u+1)N$ represents a sample size of a batch after augmenting, comprising augmented samples, samples of a same category and samples of different categories, $y_i$ represents a category label of a sample i, $y_j$ represents a category label of a sample j, $y_k$ represents a category label of a sample k, $\|Z_i^{norm}\|$ represents a norm of a vector $Z_i^{norm}$, $\|Z_j^{norm}\|$ represents a norm of a vector $Z_j^{norm}$, $E_{ij}$ represents a cosine distance between the sample i and the sample j, and $E_{ik}$ represents a cosine distance between the sample i and the sample k; and
wherein the augmented similarity measure item is calculated as follows:

$$s^A(Z^{norm}, Z'^{norm}) = \frac{-1}{2(u+1)N} \sum_{j}^{2(u+1)N} 1_{i \ne j} 1_{A_i = A_j} \log \frac{E_{ij}}{\sum_{k}^{2(u+1)N} 1_{i \ne k} 1_{A_i \ne A_k} E_{ik}}$$

where $A_i$ represents an augmented label of the sample i, $A_i = A_j$ represents that the sample i and the sample j are obtained by augmenting a same sample, and $A_i \ne A_k$ represents that the sample i and the sample j are obtained by augmenting different samples.

7. The system for predicting end-stage renal disease complication risk based on contrastive learning according to claim 5, wherein the complication risk prediction model constructing unit comprises:
- a complication risk prediction model defining component, configured to define a network structure of an end-stage renal disease complication risk prediction network, and select an activation function and a loss function of the end-stage renal disease complication risk prediction network and an optimization method; and
- a complication risk prediction model optimizing component, configured to train the complication risk prediction network using the optimization method, to complete constructing of the complication risk prediction model.

* * * * *